(12) United States Patent
Sun et al.

(10) Patent No.: US 11,208,484 B2
(45) Date of Patent: Dec. 28, 2021

(54) USE OF COMBINATION OF ANTI-PD-1 ANTIBODY AND VEGFR INHIBITOR IN PREPARATION OF DRUG FOR TREATING CANCERS

(71) Applicants: Suzhou Suncadia Biopharmaceuticals Co., Ltd., Jiangsu (CN); Jiangsu Hengrui Medicine Co., Ltd., Jiangsu (CN)

(72) Inventors: Xing Sun, Jiangsu (CN); Guoqing Cao, Jiangsu (CN); Changyong Yang, Jiangsu (CN); Lianshan Zhang, Jiangsu (CN); Yong Guo, Jiangsu (CN)

(73) Assignees: Suzhou Suncadia Biopharmaceuticals Co., Ltd., Jiangsu (CN); Jiangsu Hengrui Medicine Co., Ltd., Jiangsu (CN)

( * ) Notice: Subject to any disclaimer, the term of this patent is extended or adjusted under 35 U.S.C. 154(b) by 167 days.

(21) Appl. No.: 16/339,819

(22) PCT Filed: Oct. 9, 2017

(86) PCT No.: PCT/CN2017/105410
§ 371 (c)(1),
(2) Date: Apr. 5, 2019

(87) PCT Pub. No.: WO2018/068691
PCT Pub. Date: Apr. 19, 2018

(65) Prior Publication Data
US 2020/0040078 A1    Feb. 6, 2020

(30) Foreign Application Priority Data
Oct. 10, 2016   (CN) .......................... 201610884688.3

(51) Int. Cl.
| | | |
|---|---|---|
| C07K 16/28 | (2006.01) | |
| A61P 35/00 | (2006.01) | |
| A61K 9/00 | (2006.01) | |
| A61K 31/444 | (2006.01) | |
| A61K 39/395 | (2006.01) | |
| A61K 39/00 | (2006.01) | |

(52) U.S. Cl.
CPC ........ *C07K 16/2818* (2013.01); *A61K 9/0053* (2013.01); *A61K 31/444* (2013.01); *A61K 39/3955* (2013.01); *A61P 35/00* (2018.01); *A61K 2039/505* (2013.01); *A61K 2039/54* (2013.01); *A61K 2039/545* (2013.01); *C07K 2317/24* (2013.01); *C07K 2317/565* (2013.01)

(58) Field of Classification Search
CPC ........... C07K 16/2818; C07K 2317/24; C07K 2317/565; C07K 16/28; A61P 35/00; A61K 9/0053; A61K 31/444; A61K 39/3955; A61K 2039/505; A61K 2039/54; A61K 2039/545; A61K 39/395; A61K 45/06; A61K 2300/00
See application file for complete search history.

(56) References Cited

U.S. PATENT DOCUMENTS

2015/0218274 A1 *  8/2015  Sabatos-Peyton et al. .................. C07K 6/28

FOREIGN PATENT DOCUMENTS

| CA | 2934073 A1 | 6/2015 | |
|---|---|---|---|
| CN | 101675930 A | 3/2010 | |
| CN | 101676267 A | 3/2010 | |
| CN | 105801476 A * | 7/2016 | ........... C07D 213/82 |
| WO | 2015088847 A1 | 6/2015 | |
| WO | WO 2015/085847 A1 * | 6/2015 | ............. C07K 16/28 |
| WO | WO2015085847 A1 * | 6/2015 | ............. C07K 16/28 |
| WO | 2015119930 A1 | 8/2015 | |
| WO | WO 2016/054555 A2 * | 4/2016 | ............. A61K 31/00 |

OTHER PUBLICATIONS

Jiangsu HengRui Medicine Co., Ltd.; Study of Apatinib After Systemic Therapy in Patients With Hepatocellular Carcinoma(AHELP); Clinical Trials; NCT02329860; Jan. 1, 2015 (Year: 2015).*
Hu X, Cao J, Hu W, Wu C, Pan Y, Cai L, Tong Z, Wang S, Li J, Wang Z, Wang B, Chen X, Yu H. Multicenter phase II study of apatinib in non-triple-negative metastatic breast cancer. BMC Cancer. Nov. 7, 2014;14:820 (Year: 2014).*
Int'l Search Report and Written Opinion dated Jan. 15, 2018 in Int'l Application No. PCT/CN2017/105410.
Patnaik et al., "Phase I Study of Pembrolizumab (MK-3475; Anti-PD-1 Monoclonal Antibody) in Patients with Advanced Solid Tumors," Clinical Cancer Research, vol. 21, No. 19, pp. 4286-4293 (Oct. 1, 2015).
Huang et al., "Phase I study of the anti-PD-1 antibody SHR-1210 in patients with advanced solid tumors," Journal of Clinical Oncology, vol. 35, No. 15_suppl, p. e15572 (May 2017).
Li et al., "Randomized, Double-Blind, Placebo-Controlled Phase III Trial of Apatinib in Patients With Chemotherapy-Refractory Advanced or Metastatic Adenocarcinoma of the Stomach or Gastroesophageal Junction," Journal of Clinical Oncology, vol. 34, No. 13, pp. 1448-1454 (May 1, 2016).

* cited by examiner

*Primary Examiner* — Hong Sang
*Assistant Examiner* — Sung Min Yoon
(74) *Attorney, Agent, or Firm* — Ice Miller LLP

(57) ABSTRACT

Disclosed is the use of a combination of an anti-PD-1 antibody and a VEGFR inhibitor in the preparation of a drug for treating cancers.

9 Claims, 2 Drawing Sheets
Specification includes a Sequence Listing.

USE OF COMBINATION OF ANTI-PD-1 ANTIBODY AND VEGFR INHIBITOR IN PREPARATION OF DRUG FOR TREATING CANCERS

CROSS-REFERENCE TO RELATED APPLICATION

This application is a Section 371 of International Application No. PCT/CN2017/105410, filed Oct. 9, 2017, which was published in the Chinese language on Apr. 19, 2018, under International Publication No. WO 2018/068691 A1, which claims priority under 35 U.S.C. § 119(b) to Chinese Application No. 201610884688.3, filed Oct. 10, 2016, the disclosures of which are incorporated herein by reference in their entirety.

REFERENCE TO SEQUENCE LISTING SUBMITTED ELECTRONICALLY

This application contains a sequence listing, which is submitted electronically via EFS-Web as an ASCII formatted sequence listing with a file name "Sequence Listing_688452_108US" and a creation date of Mar. 17, 2019, and having a size of 7.1 kb. The sequence listing submitted via EFS-Web is part of the specification and is herein incorporated by reference in its entirety.

FIELD OF THE INVENTION

The present invention relates to the use of a combination of an anti-PD-1 antibody and a VEGFR inhibitor in the preparation of a medicament for the treatment of cancer.

BACKGROUND OF THE INVENTION

PD-1 antibodies specifically recognize and bind to PD-1 on the surface of lymphocytes, which leads to the blockade of PD-1/PD-L1 signaling pathway. This in turn activates the immune cytotoxicity of T cells against tumors and modulates the immune system of the body to eliminate tumor cells in vivo. WO201508584 discloses a novel anti-PD-1 antibody, which is currently in clinical trials and has shown an anti-tumor effect.

Apatinib is the first oral anti-angiogenic drug for advanced gastric cancer in the world, which is highly selective for VEGFR-2 and has a potent anti-angiogenic effect. In a multicenter, randomized, double-blind, placebo-controlled phase III clinical trial of apatinib in patients with metastatic gastric/gastroesophageal junction cancer after receiving second line therapy, the results showed that, when compared with placebo, apatinib alone could prolong median overall survival by 1.8 months, median progression-free survival by 0.8 months, and adverse events were controllable (Randomized, Double-Blind, Placebo-Controlled Phase III Trial of apatinib in Patients With Chemotherapy-Refractory Advanced or Metastatic Adenocarcinoma of the Stomach or Gastroesophageal Junction. J Clin Oncol, 2016 Feb. 16). The structural formula of apatinib is as shown in formula (I).

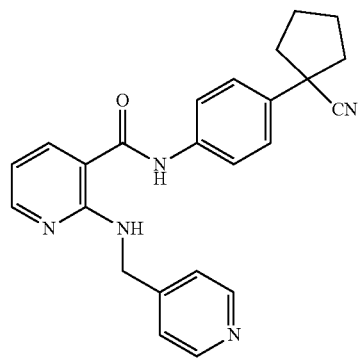

Formula (I)

CN101676267A discloses a series of salts of apatinib, such as mesylate, hydrochloride, and the like. The preclinical animal experiments disclosed in CN101675930A also show that apartinib combined with cytotoxic drugs such as oxaliplatin, 5-Fu, docetaxel and doxorubicin can significantly improve the therapeutic effect.

At present, no combinational use of a PD-1 antibody and a VEGFR inhibitor has been approved for marketing, but multiple PD-1 antibodies (from other companies) and VEGFR inhibitors (such as sunitinib, sorafenib, etc.) are in phase II/III clinical trial, and the indications are respectively malignant liver cancer (sorafenib combined with PD-1 antibody) and metastatic renal cell carcinoma (sunitinib combined with PD-1 antibody). The preliminary results showed that the combinations of two drugs are more effective and better than the single drug.

WO2015119930 discloses the use of a PD-1 antibody in combination with axitinib, and WO2015088847 discloses the use of a PD-1 antibody in combination with pazopanib. However, the action mechanism of these VEGFR inhibitors, including sorafenib, sunitinib, axitinib and pazopanib, differ from that of apatinib. Apatinib has the strongest inhibitory effect on VEGFR-2, but it has little or no inhibition on other kinases, that is, apatinib is highly selective for VEGFR-2. Therefore, the disease treated by apatinib is also different from the aforementioned drugs, and whether apatinib can synergize with a PD-1 antibody and improve its efficacy need to be further studied. In addition, according to a current clinical study of a PD-1 antibody administered alone (Phase I study of the anti-PD-1 antibody SHR-1210 in patients with advanced solid tumors. (2017): e15572-e15572), the incidence of capillary hemangioma was as high as 79.3%, the incidence of hypothyroidism was 29.3%, the incidence of pruritus was 19.0%, and the incidence of diarrhea was 10.3%. Such high incidence of adverse effects undoubtedly put a burden on the mental health and quality of life of cancer patients; therefore, it is very important to reduce adverse effects during drug administration.

SUMMARY OF THE INVENTION

The present invention provides use of a combination of an anti-PD-1 antibody and a VEGFR inhibitor in the preparation of a medicament for the treatment of cancer.

Preferably, the VEGFR inhibitor is a VEGFR-2 inhibitor.

A preferred VEGFR inhibitor of the present invention is a VEGFR inhibitor which has an IC50 of less than 100 nM for VEGFR kinase and has no inhibitory activity against EGFR, HER2, FGFR (IC50>10000 nM), according to the test method disclosed in CN101676267A. A particularly preferred VEGFR inhibitor is a VEGFR-2 inhibitor having an IC50 of less than 50 nM for VEGFR-2 kinase, preferably less than 20 nM, more preferably less than 10 nM, and most preferably less than 5 nM, and the inhibitory effect thereof on VEGFR-1 or VEGFR-3 is poor, for example, its IC50 is greater than 20 nM, preferably greater than 50 nM.

In a preferred embodiment of the present invention, the VEGFR-2 inhibitor is apatinib or a pharmaceutically acceptable salt thereof.

The anti-PD-1 antibody is known, and preferably the light chain variable region of the anti-PD-1 antibody comprises LCDR1, LCDR2 and LCDR3 as shown in SEQ ID NO: 4, SEQ ID NO: 5 and SEQ ID NO: 6, respectively.

The heavy chain variable region of the anti-PD-1 antibody comprises HCDR1, HCDR2 and HCDR3 as shown in SEQ ID NO: 1, SEQ ID NO: 2 and SEQ ID NO: 3, respectively.

Wherein the CDR sequences described above are shown in the following table:

| Name  | Sequence        | NO.          |
|-------|-----------------|--------------|
| HCDR1 | SYMMS           | SEQ ID NO: 1 |
| HCDR2 | TISGGGANTYYPDSVKG | SEQ ID NO: 2 |
| HCDR3 | QLYYFDY         | SEQ ID NO: 3 |
| LCDR1 | LASQTIGTWLT     | SEQ ID NO: 4 |
| LCDR2 | TATSLAD         | SEQ ID NO: 5 |
| LCDR3 | QQVYSIPWT       | SEQ ID NO: 6 |

Preferably, the anti-PD-1 antibody is a humanized antibody.

The preferred humanized antibody light chain sequence is the sequence as shown in SEQ ID NO: 8 or a variant thereof; the variant preferably has 0-10 amino acid substitution(s) in the light chain variable region; more preferably, has the amino acid change of A43S.

The humanized antibody heavy chain sequence is the sequence as shown in SEQ ID NO: 7 or a variant thereof, the variant preferably has 0-10 amino acid substitution(s) in the heavy chain variable region; more preferably, has the amino acid change of G44R.

Particularly preferred, the humanized antibody light chain sequence is the sequence as shown in SEQ ID NO: 8, and the heavy chain sequence is the sequence as shown in SEQ ID NO: 7.

The sequences of the aforementioned humanized antibody heavy and light chains are as follows:

Heavy chain
SEQ ID NO: 7
EVQLVESGGGLVQPGGSLRLSCAASGFTFSSYMMSWVRQAPGKGLEWV

ATISGGGANTYYPDSVKGRFTISRDNAKNSLYLQMNSLRAEDTAVYYC

ARQLYYFDYWGQGTTVTVSSASTKGPSVFPLAPCSRSTSESTAALGCL

VKDYFPEPVTVSWNSGALTSGVHTFPAVLQSSGLYSLSSVVTVPSSSL

GTKTYTCNVDHKPSNTKVDKRVESKYGPPCPPCPAPEAAGGPSVFLFP

PKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHY

TQKSLSLSLGK

Light chain
SEQ ID NO: 8
DIQMTQSPSSLSASVGDRVTITCLASQTIGTWLTWYQQKPGKAPKLLI

YTATSLADGVPSRFSGSGSGTDFTLTISSLQPEDFATYYCQQVYSIPW

TFGGGTKVEIKRTVAAPSVFIFPPSDEQLKSGTASVVCLLNNFYPREA

KVQWKVDNALQSGNSQESVTEQDSKDSTYSLSSTLTLSKADYEKHKVY

ACEVTHQGLSSPVTKSFNRGEC

In a preferred embodiment of the present invention, the VEGFR inhibitor can also be selected from the group consisting of MP-0250, DE-120, ALN-VSP, Aflibercept, Anecortave, BI-695502, Bevacizumab, PF-06439535, Carboxyamidotriazole, Vanucizumab, RG-7716, Bevacizumab analogue, Navicixizumab, Ranibizumab, Ranibizumab analogue, Conbercept, IBI-302, BI-836880, ARQ-736, RPI-4610, LMG-324, PTC-299, ABT-165, AG-13958, Brolucizumab, PAN-90806, Vatalanib, ODM-203, Altiratinib, TG-100572, OPT-302, TG-100801, CEP-7055, TAS-115, Ilorasertib, Foretinib, JNJ-26483327, Metatinib, R-1530, Tafetinib, Vorolanib, Donafenib, Subutinib, Regorafenib, VGX-100, ENMD-2076, Anlotinib, Ningetinib, Tesevatinib, Tanibirumab, Lucitanib, Cediranib, Chiauranib, IMC-3C5, Glesatinib, KRN-633, Icrucumab, PF-337210, RAF265, Puquitinib, SU-014813, Tivozanib, Fruquintinib, Sitravatinib, Pegaptanib, Pazopanib, Vandetanib, Axitinib, Sulfatinib, Ramucirumab, Plitidepsin, Orantinib, Alacizumab pegol, Telatinib, Ponatinib, Cabozantinib, Lenvatinib, Brivanib Alaninate, and Linifanib.

In the use of the present invention, the cancer is preferably a cancer expressing PD-L1; more preferably is breast cancer, lung cancer, gastric cancer, intestinal cancer, renal cancer, liver cancer, melanoma, or non-small cell lung cancer; most preferably is non-small cell lung cancer, melanoma and kidney cancer, or intestinal cancer, and the intestinal cancer includes colon cancer, colorectal cancer, and the like.

Apatinib is preferably administered in the form of pharmaceutically acceptable salt when being administered. The pharmaceutically acceptable salt can be selected from the group consisting of mesylate and hydrochloride.

Specifically, when being administered, the anti-PD-1 antibody can be administered at a dose of 0.5-30 mg/kg, preferably 2-10 mg/kg, more preferably 2-6 mg/kg, and most preferably 3 mg/kg It can be administered once every 1 to 3 weeks, preferably once every 2 weeks. For adult humans, a fixed dose can also be used, for example 100-1000 mg per administration, preferably 200-600 mg. The dose of the VEGFR inhibitor can be 3-200 mg/kg. For adult humans, a fixed dose can also be used, for example 100-1000 mg, 250-1000 mg, preferably 400-850 mg, 100-500 mg, it can be administered once per day.

In the present invention, the term "combination" is a mode of administration, including various situations, in which two drugs are administered sequentially or simultaneously. Herein, so-called "simultaneously" refers to the administration of the anti-PD-1 antibody and the VEGFR inhibitor during the same administration cycle For example, administration of the two drugs within 2 days or within 1 day. So-called "sequentially" administrated includes the administration of the anti-PD-1 antibody and the VEGFR inhibitor in different administration cycles, respectively.

These modes of administration all belong to the combination administration described in the present invention.

In a preferred embodiment of the present invention, the anti-PD-1 antibody is administered by injection, for example, subcutaneously or intravenously, and the anti-PD-1 antibody is formulated in an injectable form prior to injection. A particularly preferred injectable form of the anti-PD-1 antibody is injection or a lyophilized powder comprising the anti-PD-1 antibody, buffer, stabilizer, and optionally comprising surfactant. The buffer can be selected from one or more of acetate, citrate, succinate and phosphate. The stabilizer can be selected from sugars or amino acids, preferably disaccharide such as sucrose, lactose, trehalose and maltose. The surfactant is selected from the group consisting of polyoxyethylene hydrogenated castor oil, glycerin fatty acid ester, polyoxyethylene and sorbitan fatty acid ester; preferably the polyoxyethylene sorbitan fatty acid ester is polysorbate 20, 40, 60 or 80; most preferred is polysorbate 20. The most preferred injectable form of the anti-PD-1 antibody comprises anti-PD-1 antibody, acetate buffer, trehalose and polysorbate 20.

The present invention provides the anti-PD-1 antibody as described above in combination with the VEGFR as described above, as a medicament for treating tumors.

The present invention provides the anti-PD-1 antibody as described above in combination with the VEGFR as described above as a medicament for reducing adverse effect of drugs. Preferably, the adverse effect of drugs is selected from the effect caused by the anti-PD-1 antibody or the VEGFR inhibitor.

The present invention provides the anti-PD-1 antibody as described above in combination with the VEGFR inhibitor as described above, as a medicament for reducing the dose of the anti-PD-1 antibody administered alone and/or the dose of the VEGFR inhibitor administered alone.

The present invention provides a method for treating tumors/cancer comprising administering to a patient the anti-PD-1 antibody as described above and the VEGFR inhibitor as described above.

The present invention provides a method for reducing the dose of either the anti-PD-1 antibody or the VEGFR inhibitor administered alone, comprising administering to a patient the anti-PD-1 antibody as described above in combination with the VEGFR inhibitor as described above.

Preferably, when administered in combination with the anti-PD-1 antibody, the VEGFR inhibitor is administered at a dose of 10% to 100%, preferably 10% to 75%, more preferably 75%, 50%, 25%, 12.5% of the dose administered alone.

Preferably, when administered in combination with the VEGFR inhibitor, the anti-PD-1 antibody is administered at a dose of 10% to 100%, preferably 10% to 50% of the dose administered alone.

In a preferred embodiment of the present invention, when the anti-PD-1 antibody is administered in combination with the VEGFR inhibitor, the adverse effect of drugs mediated by the anti-PD-1 antibody and/or the immune system can be reduced; preferably, the adverse effect is selected from the group consisting of a vascular-associated adverse effect, glandular hypofunction, skin adverse effect, respiratory system adverse effect, liver-associated adverse effect, endocrine-associated adverse effect, digestive system adverse effect, kidney-associated adverse effect, fatigue, and pyrexia. The preferred vascular-associated adverse effect is selected from the group consisting of hemangioma, vasculitis, and lymphangioma; the glandular hypofunction is selected from the group consisting of hypothyroidism, hypoparathyroidism, pancreatic hypofunction, and prostatic hypofunction; the skin adverse effect is selected from the group consisting of pruritus, urticaria, rash, and toxic epidermal necrosis; the respiratory adverse effect is selected from the group consisting of pneumonia, bronchitis, chronic obstructive pulmonary disease, and pulmonary fibrosis; the liver-associated adverse effect is selected from the group consisting of hepatitis and liver dysfunction; the endocrine-associated adverse effect is selected from the group consisting of diabetes type I, diabetes type II, and hypoglycemia; the kidney-associated adverse effect is selected from the group consisting of nephritis and renal failure; the digestive system adverse effect is selected from the group consisting of diarrhea, nausea, emesis, enteritis, and constipation. More preferably, the adverse effect of drugs is selected from the group consisting of hemangioma, hypothyroidism, hypoparathyroidism, pruritus, pneumonia, hepatitis, liver dysfunction, diabetes type I, nephritis, and renal failure.

The present invention provides a pharmaceutical kit or a pharmaceutical package, comprising the VEGFR inhibitor and the anti-PD-1 antibody as described above.

DETAILED DESCRIPTION OF THE INVENTION

Figure 1:
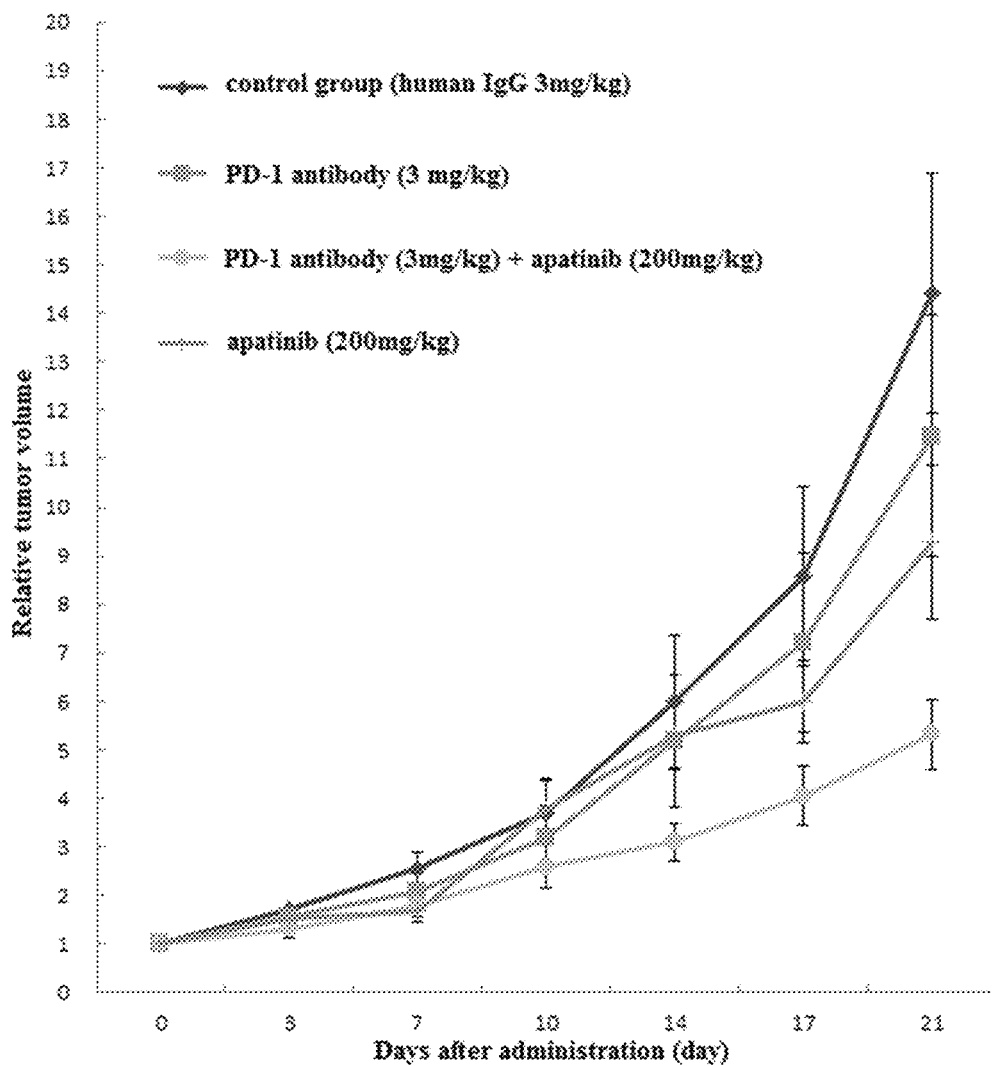
FIG. 1. Effect of administration of antibody and compound on the relative volume of MC38 (PD-L1) xenograft in tumor-bearing mice.

The present invention is further described below in conjunction with the examples. These examples are not intended to limit the scope of the present invention.

Example 1: Effect of the Anti-PD-1 Antibody and Apatinib Mesylate, Administered Alone or in Combination, on Human PD-1 Transgenic C57 Mice which Bear Mouse Colon Cancer Cell MC-38 (PD-L1) Xenograft Transferred with PD-L1 Gene 1. Study Purposes Human PD-1 transgenic mice were used as test animals. The effects of anti-PD-1 antibody in combination with apartinib on human PD-1 expressed in transgenic C57 mice were evaluated, and the transgenic mice bear mouse colon cancer cell MC-38 (PD-L1) xenograft transfected with PD-L1 gene.

2. Test Antibodies and Compounds

The anti-PD-1 antibody was prepared according to the method disclosed in WO2015085847 in which the corresponding code of the antibody is H005-1, and the sequences of the heavy and light chain are shown in SEQ ID NO: 7 and SEQ ID NO: 8 in the present invention. Lot number: P1512, 200 mg/vial, formulated into 20 mg/ml before use.

Apatinib mesylate was prepared according to the method disclosed in CN101676267A, lot number: 668160401; molecular weight: 493.58; purity: 99.60%.

3. Experimental Animals

Human PD-1 transgenic C57 mice, specific-pathogen-free (SPF), with different body weights, 50% male and 50% female, were purchased from IsisInnovation Limited, UK.

4. Drug Preparation

Anti-PD-1 antibody (3 mg/kg): anti-PD-1 antibody stock solution (20 mg/ml) was adjusted to a concentration of 0.3 mg/ml with phosphate buffered saline (PBS), and the intraperitoneal injection volume was 0.2 ml/mouse.

Apatinib (200 mg/kg): 400 mg apatinib was dissolved in 20 ml of 0.5% sodium carboxymethylcellulose (NaCMC), adjusted to 20 mg/ml, and was administered in 0.2 ml per mouse by gavage.

The solvent vehicle (HIgG) control contained human IgG (3 mg/kg dissolved in 0.5% CMC, adjusted to 0.3 mg/ml, and the volume for intraperitoneal injection was 0.2 ml/mouse.

5. Test Method 5.1 C57 Mice were Adapted to the Laboratory Environment for >5 Days.

5.2 Tumor Cells Transplantation

Skin preparation was performed on human PD-1 transgenic C57 mice one day before MC38 (PD-L1) cells ($5\times10^6$/mouse) were inoculated subcutaneously at the right flank on June 12. The tumors were then grown for 8 days. When the tumors reached $142.17\pm13.30$ mm$^3$, the animals were randomly assigned to 4 groups (d0) with 8 mice in each group (four male mice and four female mice in each group).

5.3 Dose and Method of Administration

Anti-PD-1 antibody was injected intraperitoneally, Q2D*7 (once every 2 days, 7 times in total), and apatinib was administered by oral gavage, QD*14 (once a day for 14 days). The specific drug administration regimen is shown in Table 1.

5.4 Determination of Volume of Xenograft and Body Weight of Mice

Tumor volume and body weight were measured twice a week and data were recorded.

5.5 Statistics

Excel 2003 statistical software was used: the mean was calculated by avg; the SD value was calculated by STDEV; the SEM value was calculated by STDEV/SQRT; the P value indicating the difference between groups is calculated by TTEST.

The formula for calculating tumor volume (V) is:

$$V=\tfrac{1}{2}\times L_{long}\times L_{short}^2$$

Relative volume(RTV)=$V_T/V_0$

Tumor inhibition rate(%)=$(C_{RTV}-T_{RTV})/C_{RTV}$(%)

Wherein, $V_0$ and $V_T$ are the tumor volume at the beginning of the experiment and at the end of the experiment, respectively. $C_{RTV}$ and $T_{RTV}$ are the relative tumor volumes of the blank control group and the experimental group at the end of the experiment, respectively.

6. Test Results

Figure 2:
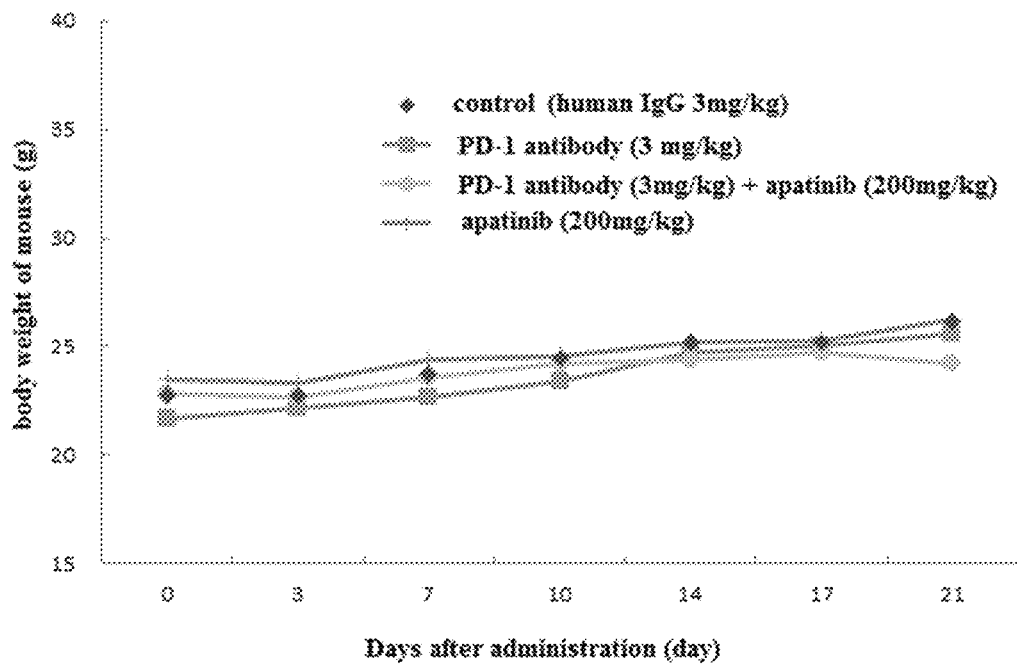
FIG. 2. Effect of administration of antibody and compound on body weight of tumor-bearing mice with MC38 (PD-L1) xenograft, wherein*indicates p<0.05, vs blank control group.
Figure 3:
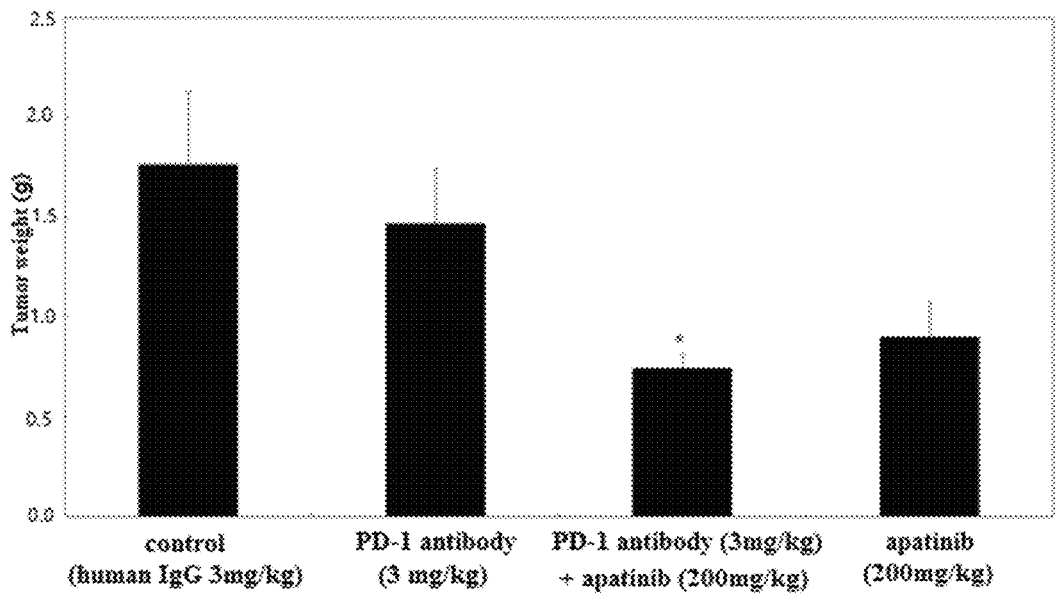
FIG. 3. Effect of administration of antibody and compound on MC38 (PD-L1) xenograft in tumor-bearing mice-tumor weight.

The PD-1 antibody was injected intraperitoneally, Q2D*7, and compound apatinib was administered by oral gavage, QD*14. On day 21 after the initial administration, the tumor inhibition rate of the group administered with the anti-PD-1 antibody (3 mg/kg) alone was 20.40%, and the tumor inhibition rate of the group administered with apatinib (200 mg/kg) alone was 35.67%. The tumor inhibition rate of the combination of the anti-PD-1 antibody (3 mg/kg) and apatinib (200 mg/kg) was 63.07% (significantly different from that in human IgG control group) There were no significant differences between the other administration groups (administration of agent alone) relative to the human IgG control group. From the experimental results, the efficacy of the combination group of the anti-PD-1 antibody (3 mg/kg)+apatinib (200 mg/kg) is superior to that of the anti-PD-1 antibody administrated alone and that of apintinib administrated alone. The body weight of mice in each group was normal, indicating that the drug had no obvious side effects. The specific data are shown in Table 1 and FIGS. 1-3.

Example 2: Clinical Study of Anti-PD-1 Antibody Combined with Apatinib Mesylate in the Treatment of Advanced Malignant Tumor Inclusion criteria: (1) advanced malignancy; (2) failure in chemotherapy by using first-line, second-line or above; (3) measurable lesions; (4) ECOG score 0-1.

Test drugs: commercially available apatinib mesylate tablet; the anti-PD-1 antibody of Example 1.

Method of administration: Up to Sep. 20, 2017, a total of 31 subjects were screened, 30 subjects were enrolled (14 subjects withdrew from treatment, and 16 subjects were still in the group of administration).

Administration method for subjects No. 001-005 was intravenous infusion of anti-PD-1 antibody, 3 mg/kg, once every 2 weeks; apatinib orally, 500 mg, once a day. Administration method for subjects No. 006-010 was intravenous infusion of anti-PD-1 antibody, 200 mg, once every 2 weeks; apatinib orally, 125 mg, once a day. Administration method for subjects No. 011-031 was intravenous infusion of anti-PD-1 antibody, 200 mg, once every 2 weeks; apatinib orally, 250 mg, once a day.

Clinical Outcome: In terms of effectiveness, in the 6$^{th}$ week, there were 24 evaluable data for efficacy evaluation, with a disease control rate (DCR) of 83.3% (20/24); in the 12th week, there were 19 evaluable data for efficacy evaluation, with a DCR of 63.2% (12/19); in the 18th week, there were 10 evaluable data for efficacy evaluation, with a DCR of 70% (7/10); in the 24$^{th}$ week, there were 5 evaluable data for efficacy evaluation, with a DCR of 80% (4/5); up to Sep. 20, 2017, there were 2 hepatocellular carcinoma subjects with their 24-week effect of partial response (PR) and progression-free survival (PFS) of more than 6 months. Among the 24 evaluable data, there were 4 cases showing optimal efficacy with PR, 15 cases of stable disease (SD), and 5 cases of progressive disease (PD). Although the objective response rate (ORR) was only 16.7%, the DCR was high, e.g., as high as 79%, and some subjects had a PFS of more than 6 months. The specific results are shown in Table 2, Table 3 and Table 4. In addition, the dose of apatinib alone in treatment of solid tumor (such as gastric cancer, gastroesophageal junction adenocarcinoma, liver cancer, etc.) was usually up to 850 mg/day (see instructions for apatinib). However, in embodiments of the invention the combination of apatinib and anti-PD-1 antibody makes it possible to reduce the dose of apatinib down to 125 mg/day, and provides improved effectiveness and better safety when compared with apatinib administrated alone. In terms of safety, up to September 20, 11 cases of serious adverse events (SAE) were reported in 8 subjects, and the incidence of SAE was 26.7% (8/30). Seven of the SAEs were observed in subjects No. 001-005 (wherein the dose of apatinib for initial test was high, 500 mg) and accounted for most of the serious adverse events. However, with modified dosage regimen, it was found that good anti-tumor effect could be maintained, and the adverse effects caused by high dose of apintinib could be significantly reduced. In addition, in this clinical study it was surprisingly found that the combination of apatinib and anti-PD-1 antibody showed almost no hemangioma-associated adverse effect in the treatment of malignant tumors when compared with anti-PD-1 antibody alone. Hemangiomas was observed in only one subject who was administrated with PD-1 antibody alone, due to intolerance to combination therapy.

Example 3: Phase II Clinical Study of Anti-PD-1 Antibody Combined with Apatinib Mesylate in the Treatment of Advanced Non-Small Cell Lung Cancer Inclusion criteria: (1) advanced non-small cell lung cancer; (2) failure in chemotherapy by using first-line or second-line or above; (3) measurable lesions; (4) ECOG score 0-1.

Test drugs: commercially available apatinib mesylate tablet; the anti-PD-1 antibody of Example 1.

Method of administration: Anti-PD-1 antibody, once every 2 weeks, intravenous infusion, 200 mg each time; apatinib mesylate orally, once daily, 250 mg or 375 mg or 500 mg each time.

Clinical results: up to July 28, a total of 15 subjects were screened, of which 12 were enrolled. A total of 12 subjects completed at least 1 cycle of administration observation, 10 patients (10/12) had disease in stable condition, and 1 patient had partial remission. See Table 5 for details. Surprisingly, it was found that the combination of apatinib mesylate and anti-PD-1 antibody enhanced the efficacy and reduced the adverse effects when compared with anti-PD-1 antibody administered alone. In this study, the common adverse effects were usually grade I to II, and the incidence of anti-PD-1 antibody-associated or immune-associated adverse effects (such as capillary hemangioma) was only 8% (1 case), the incidence of hypothyroidism was only 8% (1 case), and gastrointestinal adverse effects (such as diarrhea) and skin adverse effect (such as pruritus) were not observed. In an ASCO report published in 2017, anti-PD-1 antibody administrated alone for the treatment of solid tumors in phase I clinical trial exhibited an incidence of capillary hemangioma as high as 79.3%, and the incidence of hypothyroidism was 29.3%, the incidence of pruritus was 19.0%, the incidence of diarrhea was 10.3% (Phase I study of the anti-PD-1 antibody SHR-1210 in patients with advanced solid tumors. (2017): e15572-e15572). Therefore, the combination of apatinib mesylate and anti-PD-1 antibody can not only alleviate or control the tumor proliferation of non-small cell lung cancer (which has experienced chemotherapy failure), but also reduce the anti-PD-1 antibody-associated or immune-mediated adverse effects and improve the life quality of patients.

TABLE 1

| Group | Administration | Route | Mean tumor volume (mm$^3$) D 0 | SEM | Mean tumor volume (mm$^3$) D 21 | SEM | Relative tumor volume D 21 | SEM | % Tumor inhibition rate D 21 | P (vs blank) | Number of animals/group |
|---|---|---|---|---|---|---|---|---|---|---|---|
| HIgG (3 mg/kg) | Q2D*7 | ip | 141.46 | 13.23 | 1983.55 | 292.09 | 14.41 | 2.07 | — | — | 8 |
| Anti-PD-1 antibody (3 mg/kg) | Q2D*7 | ip | 146.40 | 12.68 | 1652.93 | 309.61 | 11.47 | 2.49 | 20.40% | 0.379164 | 8 |
| Anti-PD-1 antibody (3 mg/kg) + apatinib (200 mg/kg) | Q2D*7/ QD(14 D) | ip/po | 146.11 | 11.69 | 771.95 | 73.42 | 5.32 | 0.73 | 63.07%** | 0.001007 | 8 |
| apatinib | QD(14 D) | po | 139.70 | 7.59 | 1263.86 | 206.54 | 9.27 | 1.58 | 25.67% | 0.068923 | 8 |

**p < 0.01, vs control group

TABLE 2

Administration methods: PD-1 antibody 3 mg/kg + apatinib 500 mg

| No. | Diagnosis | Previous therapy | Treatment cycle | 6 weeks evaluation | 12 weeks evaluation | 18 weeks evaluation | 24 weeks evaluation | 32 weeks evaluation | Optimal efficacy |
|---|---|---|---|---|---|---|---|---|---|
| 001 | gastric cancer | Second-line therapy | 1 | NA | NA | NA | NA | NA | Not evaluated |
| 002 | gastric cancer | Fouth-line therapy | 6 | SD reduced | PD | NA | NA | NA | SD |
| 003 | gastric cancer | Fifth-line therapy | 9 | SD reduced | SD reduced | PD | PD | NA | SD |
| 004 | hepatocellular carcinoma | First-line therapy | 2 | SD increased | NA | NA | NA | NA | SD |
| 005 | hepatocellular carcinoma | Second-line therapy | 1 | NA | NA | NA | NA | NA | Not evaluated |

TABLE 3

Administration methods: PD-1 antibody 200 mg + apatinib 125 mg

| No. | Diagnosis | Previous therapy | Treatment cycle | 6 weeks evaluation | 12 weeks evaluation | 18 weeks evaluation | 24 weeks evaluation | 32 weeks evaluation | Optimal efficacy |
|---|---|---|---|---|---|---|---|---|---|
| 006 | hepatocellular carcinoma | Second-line therapy | 18 | SD increased | SD increased | PD | PR | SD | PR |
| 007 | hepatocellular carcinoma | Second-line therapy | 18 | SD | SD reduced | SD reduced | SD | Performed, Not evaluated | SD |
| 009 | hepatocellular carcinoma | Second-line therapy | 18 | SD | SD reduced | SD reduced | SD reduced | NA | SD |
| 008 | hepatocellular carcinoma | First-line therapy | 4 | PD | NA | NA | NA | NA | PD |
| 010 | gastric cancer | Third-line therapy | 2 | NA | NA | NA | NA | NA | Not evaluated |

TABLE 4

Administration methods: PD-1 antibody 200 mg + apatinib 250 mg

| No. | Diagnosis | Therapy | Treatment cycle | 6 weeks evaluation | 12 weeks evaluation | 18 weeks evaluation | 24 weeks evaluation | 32 weeks evaluation | Optimal efficacy |
|---|---|---|---|---|---|---|---|---|---|
| 011 | hepatocellular carcinoma | Second-line therapy | 15 | SD reduced | PR | PR | PR | NA | PR |
| 014 | hepatocellular carcinoma | Third-line therapy | 14 | SD reduced | SD reduced | SD | Performed, Not evaluated | NA | SD |
| 019 | hepatocellular carcinoma | Second-line therapy | 11 | SD | SD reduced | SD | NA | NA | SD |
| 021 | hepatocellular carcinoma | First-line therapy | 9 | SD increased | SD | Performed, Not evaluated | NA | NA | SD |
| 027 | hepatocellular carcinoma | Second-line therapy | 3 | SD reduced | Not performed | NA | NA | NA | SD |
| 018 | hepatocellular carcinoma | Second-line therapy | 4 | SD increased | PD | NA | NA | NA | PD |
| 016 | gastric cancer | Fouth-line therapy | 9 | PR | PD | PD | NA | NA | PR |
| 025 | gastric cancer | Second-line therapy | 8 | PR | PR | NA | NA | NA | PR |
| 012 | gastric cancer | Multi-line therapy | 9 | SD reduced | SD reduced | SD increased | NA | NA | SD |
| 013 | gastric cancer | Third-line therapy | 5 | SD | NA | NA | NA | NA | SD |
| 022 | gastric cancer | Second-line therapy | 10 | SD reduced | SD | SD | NA | NA | SD |
| 024 | gastric cancer | Third-line therapy | 6 | SD increased | PD | NA | NA | NA | SD |
| 026 | gastric cancer | Third-line therapy | 8 | SD reduced | SD | NA | NA | NA | SD |
| 028 | gastric cancer | Third-line therapy | 7 | SD | Performed, Not evaluated | NA | NA | NA | SD |
| 015 | gastric cancer | Second-line therapy | 5 | 9 weeks PD | PD | NA | NA | NA | PD |
| 017 | gastric cancer | Fifth-line therapy | 4 | PD | PD | NA | NA | NA | PD |
| 023 | gastric cancer | Second-line therapy | 5 | PD | PD | NA | NA | NA | PD |
| 029 | gastric cancer | Multi-line therapy | 5 | Performed, Not evaluated | NA | NA | NA | NA | To be evaluated |
| 030 | gastric cancer | Third-line therapy | 5 | Performed, Not evaluated | NA | NA | NA | NA | To be evaluated |
| 031 | gastric cancer | Second-line therapy | 3 | Not Performed | NA | NA | NA | NA | Not evaluated |

TABLE 5

Efficacy evaluation of enrolled patients

| Screening No. | Baseline | Efficacy evaluation-Diameter (mm)/Baseline ratio (%) 2 cycles | 4 cycles | General evaluation |
|---|---|---|---|---|
| 01001 | 28 | 27/−3.6% | 15.5/−44.6% | PR |
| 01002 | 20.6 | 1 cycle, hydrothorax increased | | PD |
| 01003 | 76.7 | New onset of hydrothorax | 74.7/−2.6% | SD |
| 01005 | 122.9 | liver metastases increased, enlarged | | PD |
| 01006 | 137 | 118/−13.9% | 107/−22% | SD |
| 01007 | 134.2 | 117.7/−12.2% | 107/−20.3 | SD |
| 01008 | 58.3 | 52/−10.8% | SD | SD |
| 01010 | 11 | 9/−20% | | SD |
| 01011 | 36 | SD | | SD |
| 01013 | 87 | SD | | SD |
| 01014 | 85.5 | SD | | SD |
| 01015 | | SD | | SD |

We claim:

1. A method of reducing an adverse effect of an anti-PD-1 antibody in a subject in need of a treatment of a cancer, the method comprising administering to the subject, an anti-PD-1 antibody and apatinib or the pharmaceutically acceptable salt thereof, wherein the adverse effect comprises at least hemangiomas, and the anti-PD-1 antibody comprises:
   an antibody light chain variable region comprising LCDR1, LCDR2 and LCDR3 having the amino acid sequences of SEQ ID NO: 4, SEQ ID NO: 5 and SEQ ID NO: 6, respectively; and
   an antibody heavy chain variable region comprising HCDR1, HCDR2 and HCDR3 having the amino acid sequences of SEQ ID NO: 1, SEQ ID NO: 2 and SEQ ID NO: 3, respectively.

2. The method of claim 1, comprising administering to the subject a pharmaceutically acceptable salt of apatinib selected from the group consisting of mesylate salt of apatinib and hydrochloride salt of apatinib.

3. The method of claim 1, wherein the anti-PD-1 antibody is a humanized antibody.

4. The method of claim 3, wherein the humanized antibody comprises an antibody light chain variable region having the amino acid sequence of SEQ ID NO:8 and an antibody heavy chain variable region having the amino acid sequence of SEQ ID NO:7.

5. The method of claim 3, wherein the humanized antibody comprises an antibody light chain variable region comprising a mutant sequence of the amino acid sequence of SEQ ID NO:8 having the amino acid substitution A43S, and an antibody heavy chain variable region comprising a mutant sequence of the amino acid sequence of SEQ ID NO: 7 having the amino acid substitution G44R.

6. The method of claim 1, wherein the cancer is selected from the group consisting of breast cancer, lung cancer, liver cancer, gastric cancer, intestinal cancer, renal cancer, melanoma and non-small cell lung cancer.

7. The method of claim 6, wherein the subject has failed at least one chemotherapy prior to the administration of the anti-PD-1 antibody and apatinib or the pharmaceutically acceptable salt thereof.

8. The method of claim 1, wherein the anti-PD-1 antibody is administered at a dose of 2 mg/kg to 6 mg/kg or from 100 mg to 1000 mg per administration, and the apatinib or the pharmaceutically acceptable salt thereof is administered orally at a dose from 100 mg to 500 mg.

9. The method of claim 1, wherein the anti-PD-1 antibody is administered at a dose of 3 mg/kg body weight of the subject or 200 mg once every two weeks, and apatinib or the pharmaceutically acceptable salt thereof is administered orally at a dose of 125 mg, 250 mg, 375 mg, or any dosage in between, once daily.

* * * * *

SEQUENCE LISTING

<160> NUMBER OF SEQ ID NOS: 8

<210> SEQ ID NO 1
<211> LENGTH: 5
<212> TYPE: PRT
<213> ORGANISM: Artificial sequence
<220> FEATURE:
<223> OTHER INFORMATION: PD-1 FORM HCDR1

<400> SEQUENCE: 1

Ser Tyr Met Met Ser
1               5

<210> SEQ ID NO 2
<211> LENGTH: 17
<212> TYPE: PRT
<213> ORGANISM: Artificial sequence
<220> FEATURE:
<223> OTHER INFORMATION: PD-1 FORM HCDR2

<400> SEQUENCE: 2

Thr Ile Ser Gly Gly Gly Ala Asn Thr Tyr Tyr Pro Asp Ser Val Lys
1               5                   10                  15

Gly

<210> SEQ ID NO 3
<211> LENGTH: 7
<212> TYPE: PRT
<213> ORGANISM: Artificial sequence
<220> FEATURE:
<223> OTHER INFORMATION: PD-1 FORM HCDR3

<400> SEQUENCE: 3

Gln Leu Tyr Tyr Phe Asp Tyr
1               5

<210> SEQ ID NO 4
<211> LENGTH: 11
<212> TYPE: PRT
<213> ORGANISM: Artificial sequence
<220> FEATURE:
<223> OTHER INFORMATION: PD-1 FORM LCDR1

<400> SEQUENCE: 4

Leu Ala Ser Gln Thr Ile Gly Thr Trp Leu Thr
1               5                   10

<210> SEQ ID NO 5

```
<211> LENGTH: 7
<212> TYPE: PRT
<213> ORGANISM: Artificial sequence
<220> FEATURE:
<223> OTHER INFORMATION: PD-1 FORM LCDR2

<400> SEQUENCE: 5

Thr Ala Thr Ser Leu Ala Asp
1               5

<210> SEQ ID NO 6
<211> LENGTH: 9
<212> TYPE: PRT
<213> ORGANISM: Artificial sequence
<220> FEATURE:
<223> OTHER INFORMATION: PD-1 FORM LCDR3

<400> SEQUENCE: 6

Gln Gln Val Tyr Ser Ile Pro Trp Thr
1               5

<210> SEQ ID NO 7
<211> LENGTH: 443
<212> TYPE: PRT
<213> ORGANISM: Artificial sequence
<220> FEATURE:
<223> OTHER INFORMATION: PD-1 FORM Heavy chain

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Met Met Ser Trp Val Arg Gln Ala Pro Gly Lys Gly Leu Glu Trp Val
        35                  40                  45

Ala Thr Ile Ser Gly Gly Gly Ala Asn Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Leu Tyr Tyr Phe Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Phe Leu Gly Gly Pro Ser Val Phe Leu Phe Pro
225                 230                 235                 240
```

```
Pro Lys Pro Lys Asp Thr Leu Met Ile Ser Arg Thr Pro Glu Val Thr
                245                 250                 255
Cys Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
            275                 280                 285
Glu Glu Gln Phe Asn Ser Thr Tyr Arg Val Val Ser Val Leu Thr Val
            290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
                340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
            370                 375                 380
Asn Asn Tyr Lys Thr Thr Pro Pro Val Leu Asp Ser Asp Gly Ser Phe
385                 390                 395                 400
Phe Leu Tyr Ser Arg Leu Thr Val Asp Lys Ser Arg Trp Gln Glu Gly
                405                 410                 415
Asn Val Phe Ser Cys Ser Val Met His Glu Ala Leu His Asn His Tyr
            420                 425                 430
Thr Gln Lys Ser Leu Ser Leu Ser Leu Gly Lys
            435                 440

<210> SEQ ID NO 8
<211> LENGTH: 214
<212> TYPE: PRT
<213> ORGANISM: Artificial sequence
<220> FEATURE:
<223> OTHER INFORMATION: PD-1 FORM Light chain

<400> SEQUENCE: 8

Asp Ile Gln Met Thr Gln Ser Pro Ser Ser Leu Ser Ala Ser Val Gly
1               5                   10                  15
Asp Arg Val Thr Ile Thr Cys Leu Ala Ser Gln Thr Ile Gly Thr Trp
            20                  25                  30
Leu Thr Trp Tyr Gln Gln Lys Pro Gly Lys Ala Pro Lys Leu Leu Ile
        35                  40                  45
Tyr Thr Ala Thr Ser Leu Ala Asp Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Val Tyr Ser Ile Pro Trp
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
```

-continued

```
Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```